(12) United States Patent
Resch

(10) Patent No.: US 8,980,172 B1
(45) Date of Patent: Mar. 17, 2015

(54) AUTOMATIC ODOR CONTROL SYSTEM AND METHOD AND RELATED SENSOR MODULE

(75) Inventor: Darrel Resch, Orlando, FL (US)

(73) Assignee: Vapex Environment Technologies, Inc., Oviedo, FL (US)

( * ) Notice: Subject to any disclaimer, the term of this patent is extended or adjusted under 35 U.S.C. 154(b) by 238 days.

(21) Appl. No.: 13/235,688

(22) Filed: Sep. 19, 2011

(51) Int. Cl.
*A61L 9/00* (2006.01)
*A62B 7/08* (2006.01)

(52) U.S. Cl.
USPC ............. 422/5; 422/4; 422/120; 422/123

(58) Field of Classification Search
USPC ......................... 422/5, 4, 120, 123
See application file for complete search history.

(56) References Cited

U.S. PATENT DOCUMENTS

| | | | |
|---|---|---|---|
| 3,659,100 A | 4/1972 | Anderson et al. | |
| 5,601,786 A * | 2/1997 | Monagan | 422/108 |
| 5,667,558 A * | 9/1997 | Bryan et al. | 95/8 |
| 5,875,722 A | 3/1999 | Gosselin, Jr. et al. | |
| 5,958,787 A | 9/1999 | Schonfeld et al. | |
| 6,076,748 A | 6/2000 | Resch et al. | |
| 6,173,602 B1 | 1/2001 | Moseley | |
| 6,447,659 B1 | 9/2002 | Peng | |
| 7,141,859 B2 | 11/2006 | DeBoer et al. | |
| 7,422,909 B2 * | 9/2008 | Schur et al. | 436/177 |
| 7,547,420 B2 * | 6/2009 | Schroder | 422/186.04 |
| 7,756,683 B2 | 7/2010 | Kilgus | |
| 8,029,726 B2 | 10/2011 | Resch et al. | |
| 2005/0262883 A1 * | 12/2005 | Yang et al. | 68/12.01 |
| 2006/0064805 A1 | 3/2006 | Yamamoto et al. | |
| 2007/0036673 A1 * | 2/2007 | Selander | 422/5 |
| 2007/0144237 A1 | 6/2007 | Moseley | |
| 2007/0269346 A1 | 11/2007 | Wohltjen | |
| 2008/0245675 A1 | 10/2008 | Joseph et al. | |
| 2009/0301382 A1 | 12/2009 | Patel | |
| 2010/0044453 A1 * | 2/2010 | Porchia et al. | 239/6 |
| 2010/0252451 A1 | 10/2010 | Warburton | |
| 2011/0024361 A1 | 2/2011 | Schwartzel et al. | |
| 2012/0024042 A1 * | 2/2012 | Vass et al. | 73/23.34 |

FOREIGN PATENT DOCUMENTS

| | | | | |
|---|---|---|---|---|
| JP | 02119998 A | * | 5/1990 | C02F 11/00 |
| JP | 2001286542 A | * | 10/2001 | A61L 9/015 |

* cited by examiner

*Primary Examiner* — Regina M Yoo
(74) *Attorney, Agent, or Firm* — Allen, Dyer, Doppelt, Milbrath & Gilchrist

(57) ABSTRACT

An odor control system includes a controlling gas source, a gas sensor module for detecting a dominant gas, the gas sensor module, a sample conduit, and an electronic control unit. The controlling gas source supplies a controlling gas to react with a foul air gas in a foul air volume. The gas sensor module for detects a dominant gas and generates a detection signal. The sample conduit routes reacted gas from the four air gas volume to the gas sensor module. The electronic control unit is configured to receive the detection signal from the gas sensor module and to automatically control the controlling gas source in response thereto. The detection signal has a signal direction relative to a signal baseline set such that the signal direction will differ depending on whether the controlling gas or the foul air gas is the dominant gas.

9 Claims, 3 Drawing Sheets

AUTOMATIC ODOR CONTROL SYSTEM AND METHOD AND RELATED SENSOR MODULE

FIELD OF THE INVENTION

This application relates to odor control systems, and more particularly, to gas sensor modules usable in connection therewith.

BACKGROUND OF THE INVENTION

Many municipal, commercial, industrial and even residential processes can generate unwanted odors. For instance, municipal water reclamation facilities and sewage treatment plants, and industrial pulp mills are often significant sources of unpleasant odors. Where such facilities are located in the vicinity of residential areas, the odor problem is compounded, although workers employed at such facilities must endure associated odors wherever located.

To address this problem, it is known to supply a controlling gas into foul air volumes at such facilities. The controlling gas reacts with foul air gases to deodorize them. One particularly effective example of this is described in U.S. Pat. No. 6,076,748, the contents of which are herein incorporated by reference in their entirety. In this example, a spray of very fine water droplets containing dissolved ozone ($O_3$) gas is injected into the foul air volume. The ozone reacts, in various forms, with the four air gases so as to oxide them, thereby eliminating the odor. In other applications, ozone is introduced directly, to the same effect, although the method described in U.S. Pat. No. 6,076,748 is believed to represent a much faster and more efficient mechanism of odor removal.

In most foul air volumes, odor production can be highly variable and unpredictable. Accordingly, it is often impractical to simply set controlling gas supply at a predetermined level or to supply the controlling gas for predetermined time periods. This type of control will typically result in either periods of insufficient controlling gas supply to effectively combat odors or excessive production of controlling gas. Currently, the most effective control of such systems is accomplished manually, based on smell. In other words, if a foul odor is prevalent, an operator raises the controlling gas supply, if the smell of ozone is prevalent, an operator lowers the controlling gas supply.

SUMMARY OF THE INVENTION

In view of the foregoing, it is an object of the present invention to provide an improved odor control system and method, and a related sensor module for use therewith. According to an embodiment of the present invention, an odor control system includes a controlling gas source, a controlling gas supply conduit, a gas sensor module for detecting a dominant gas, the gas sensor module, a sample conduit, and an electronic control unit.

The controlling gas source supplies a controlling gas to react with a foul air gas in a foul air volume. The controlling gas supply conduit routes the controlling gas from the controlling gas source to the foul air volume. The gas sensor module detects a dominant gas and generates a detection signal. The sample conduit routes reacted gas from the four air gas volume to the gas sensor module. The electronic control unit includes at least one processor adapted to execute program instructions stored in machine readable memory, and is configured to receive the detection signal from the gas sensor module and to automatically control the controlling gas source in response thereto.

The detection signal has a signal direction relative to a signal baseline. The signal baseline is set such that the signal direction will differ depending on whether the controlling gas or the foul air gas is the dominant gas.

According to a method aspect, a method of controlling odor from a foul air gas in a foul air volume using controlling gas from a controlling gas source includes arranging a gas sensor module in a sample conduit connected to the foul air volume, and setting a signal baseline of the gas sensor module. The baseline is set to correspond to a substantial absence of both the foul air gas and the controlling gas.

A dominant gas of the foul air gas and the controlling gas in the sample conduit is detected with the gas sensor module, which generates a detection signal based on the detection of the dominant gas, the detection signal having a signal direction relative to the signal baseline indicative of whether the dominant gas is the foul air gas or the controlling gas. An electronic control unit automatically controls the controlling gas source to adjust the supply of the controlling gas to the foul air volume in response to the detection signal.

According to a further aspect, the gas sensor module is located at least one reaction completion distance from the foul air volume such only the dominant gas of the foul air gas and the controlling gas will reach the gas sensor module. According to another aspect, the controlling gas is ozone and the foul air gas is hydrogen sulfide ($H_2S$). According to a further aspect, the gas sensor module includes a metal oxide sensor.

These and other objects, aspects and advantages of the present invention will be better appreciated in view of the drawings and following detailed description of preferred embodiments.

DETAILED DESCRIPTION OF PREFERRED EMBODIMENTS

Figure 1:
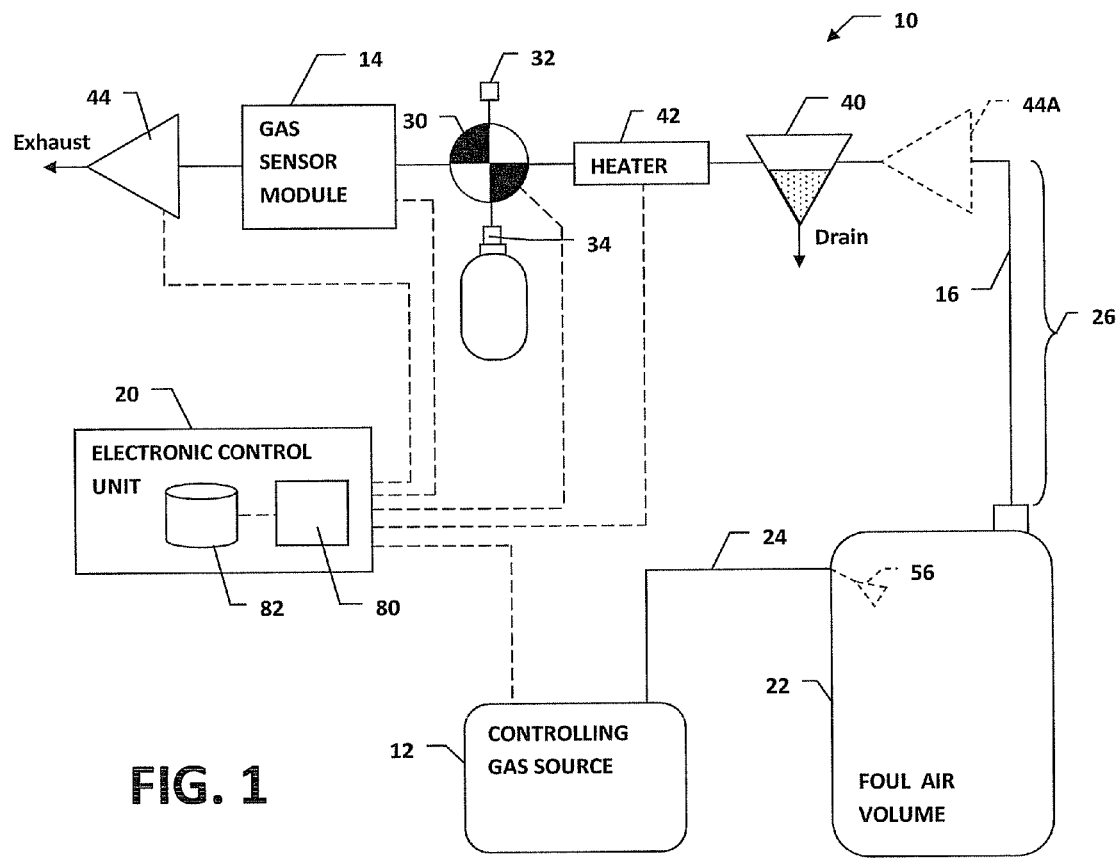
FIG. 1 is a schematic overview of an odor control system for a foul air volume, including a controlling gas source and a gas sensor module, according to an embodiment of the present invention.

Referring to FIG. 1, an odor control system 10 includes a controlling gas source 12, a gas sensor module 14 arranged in a sample conduit 16, and an electronic control unit (ECU) 20. The controlling gas source 12 supplies a controlling gas, such as ozone, to react with a foul air gas, such as hydrogen sulfide, in a foul air volume 22 via a controlling gas supply conduit 24. The gas sensor module 14 detects a dominant gas of the controlling gas and the foul air gas and generates a detection signal based on that detection. The electronic control unit 20 receives the detection signal from the gas sensor module 14 and is configured to automatically control the controlling gas 12 based thereon.

The sample conduit 16 routes gas from the foul air volume 22 to the gas sensor module 14. Preferably, gas from the foul air volume 22 travels at least one reaction completion distance 26 from where the controlling gas and foul air gas mix to ensure that the controlling gas and the foul air gas react completely only the dominant one of the two (the "dominant gas"). As used herein, "only the dominant gas" means "only one of the controlling gas and the foul air gas," not necessarily the absence of any other possible gas. Moreover, the "absence" of a gas, as used herein, does not necessarily preclude the presence of insignificant trace amounts of the gas.

To facilitate setting, monitoring, adjustment and calibration of the gas sensor module 14, a multi-position valve 30 is arranged in the sample conduit 16. The multi-position valve 30 is selectively positionable by the electronic control unit 20 to introduce gas from the foul air volume 22, a zero air port 32 or a calibration gas port 34 to the gas sensor module 14. "Zero air," as used herein, is air from which both the controlling gas and the foul air gas to sensed are absent.

To protect and facilitate proper performance of the gas sensor module 14, additional components can be arranged in the sample conduit 16, including a condensate trap 40, a heater 42 and an air pump 44. The condensate trap removes 40 removes condensed fluid from the sample conduit 16 upstream of the gas sensor module 14. The heater 42 warms the gas as necessary to an optimal temperature range for gas sensor module 14 function. The air pump 44 ensures sufficient gas volume is drawn from the foul air volume 22, and be located downstream or upstream (pump 44A in broken lines) from the gas sensor module 14. Sampled gas can be exhausted to the surroundings or routed elsewhere after passing over the gas sensor module 14. The electronic control unit 20 can be further configured to automatically control operation of the heater 42 and the air pump 44.

Figure 2:
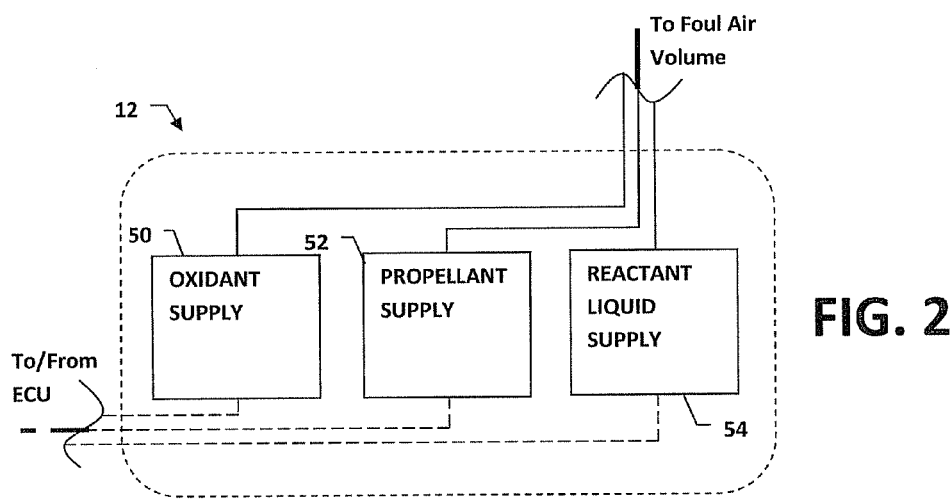
FIG. 2 is a schematic overview of the controlling gas source of FIG. 1.

Referring to FIG. 2, the controlling gas source 12 can include an oxidant supply 50, a propellant gas supply 52 for supplying pressurized atomized air or other gas, and a reactant liquid supply 54 for supplying an atomizable liquid carrier/dispersant for the oxidant. The oxidant, propellant gas and atomizable liquid are routed to a nozzle 56 or other dispersal device in the foul air volume 22 for final mixing and dispersion. It will be appreciated that other controlling gas sources can be used in connection with the present invention, although use of a controlling gas source 12 is believed to be particularly effective for odor control. It will be further appreciated that the controlling gas supply conduit 24 can be divided into different paths or channels, or formed from a plurality of individual conduits.

The electronic control unit 20 is in signal communication with each of the supplies 50, 52, 54 to control the supply of the controlling gas. Control by the electronic control unit 20 is not necessarily limited to a particular form or mechanism of control. Non-limiting examples include control of supply valves, control of supply pumps, and control of ozone generation equipment.

Figure 3:
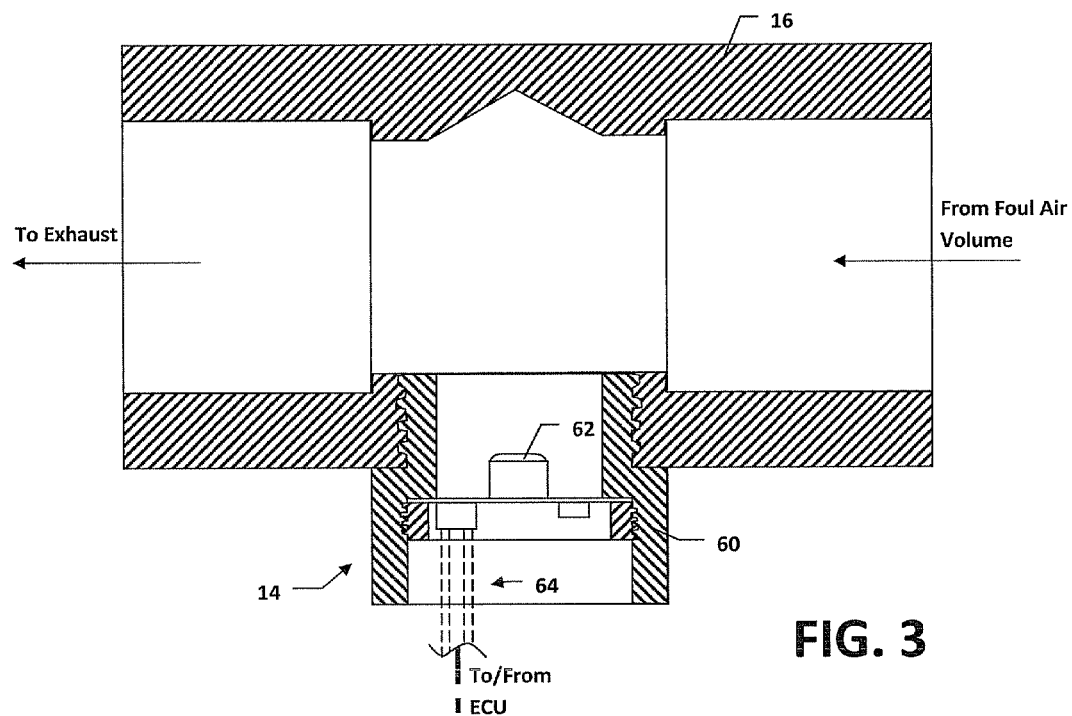
FIG. 3 is partial sectional view of the gas sensor module of FIG. 1.

Referring to FIG. 3, the gas sensor module 16 includes a sensor housing 60 connected to the sample conduit 16 with a sensor 62 arranged therein. The sensor 62 should be selected for sensitivity to both the controlling gas and the foul air gas of interest for the intended application of the odor control system 10. Sensor power and detection signal connections 64 extend from the sensor housing 60 to the electronic control module 20.

Additionally, the sensor 62 should be selected for durability under anticipated operating conditions, and have a detection time period sufficient for effective control of the intended odor control process. While not necessarily limited thereto, a metal oxide sensor has been found to be suitable for odor control applications using ozone. Certain electro-chemical cell-type sensors are also believed to be suitable.

Advantageously, the gas sensor module 16 is configured as a bi-modal sensor that is capable not only of detecting both the controlling gas and the foul air gas, but also of indicating which of the controlling gas and the foul air gas is the dominant gas. Preferably, the gas sensor module 16 should also indicate a concentration or other quantitative measure of the dominant gas.

Figure 4:
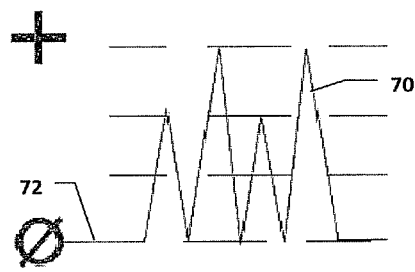
FIG. 4 is a graph of a detection signal with a first baseline.
Figure 5:
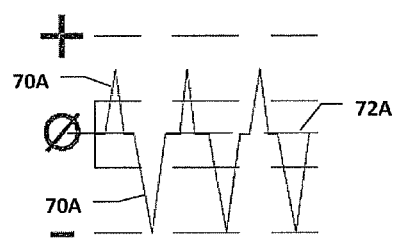
FIG. 5 is a graph of a detection signal with a second baseline, used by the gas sensor module of FIG. 1.

With reference to FIGS. 4 and 5, an example of bi-modal sensor function will be described. In the example, the response of a metallic oxide sensor to ozone and hydrogen sulfide is described, although the present invention is not necessarily limited thereto.

In FIG. 4, a detection signal 70 from a metal oxide sensor alternately exposed to ozone (the controlling gas) and hydrogen sulfide (the foul air gas) is shown. Depending on the circuit, the detection signal could represent changes in voltage or current over time. The signal baseline 72 is set so that any absorption of either ozone or hydrogen sulfide by the metal oxide sensor results in a detection signal with the same signal direction (positive, in the example). Thus, the detection signal is ambiguous as to whether the dominant gas being detected is ozone or hydrogen sulfide. As a result, the sensor output does not allow for automatic control of the controlling gas source.

In FIG. 5, the signal baseline 72A is set such that a positive signal direction of the detection signal 70A indicates that hydrogen sulfide is being detected and a negative signal direction indicates that ozone is being detected. Thus, both the identity and the concentration of the dominant gas can be determined, and the sensor output allows for automatic control of the controlling gas source.

From the foregoing, it will be appreciated that a bi-modal gas sensor module it particularly advantageous for use in connection with an odor control system, and particularly an odor control system in which ozone is used to treat hydrogen sulfide and other foul air gases. However, the bi-modal sensor of the present invention is not necessarily limited to odor control applications, and can be usefully applied in other sensing and automatic process control applications.

Referring again to FIG. 1, the electronic control unit 20 includes at least one processor 80 and machine readable memory 82. The electronic control unit 20 of the present invention is not necessarily limited to any particular number, type or configuration of processors, nor to any particular programming language, memory storage format or memory storage medium. Additionally, the electronic control unit 20 is not necessarily limited to any particular geographical location or networking or connection of the processors and/or storage media, provided that the processors and/or storage media are able to cooperate to execute the disclosed functions. The electronic control unit 20 can incorporate or allow for local, remote and/or network attachment to one or more user interface devices, including data entry and display devices.

In operation of the system 10, the gas sensor module 14 is arranged in the sample conduit 16. To initially set the baseline, or for subsequent verification or adjustment of the baseline, the electronic control unit 20 positions the multi-position valve 32 to route zero air from the zero air port 32 over the gas sensor module 16 for a predetermined time to ensure the gas sensor module 16 is clear of both the controlling gas and the foul air gas. The gas sensor module 16 response to the zero air is set as the signal baseline. Advantageously, since a bi-modal sensor is being used, this zero air flush can suffice to set the baseline signal for both controlling and foul air gases, as well as to reset the baseline signal to accommodate for sensor drift over time.

To verify gas sensor module 16 function, and to calibrate concentration measurements, the electronic control unit 20 positions the multi-position valve 32 to route gas from the calibration gas port 34 over the gas sensor module 16. Alternately attached to the calibration gas port 34, can be air flasks containing known concentrations of the controlling gas and the foul air gas. The electronic control unit 20 verifies detection signal response to the change, as well as signal direction and amplitude for each gas.

Without using the calibration gas port 34, sensor function can also be verified by the electronic control unit 20 positioning the multi-position valve 32 to route air from the foul air volume 22 over the gas sensor module 14, and then artificially driving the controlling gas source high for a predetermined period of time and securing the controlling gas source for a predetermined period of time. The electronic control unit 20 again verifies detection signal response to the change.

For automatic control, the electronic control unit 20 positions the multi-position valve 32 to route air from the foul air volume 22 over the gas sensor module 14. If, based on the signal direction of the detection signal, the controlling gas is the dominant gas, the electronic control unit 20 reduces the controlling gas supply from the controlling gas source 12 to the foul air volume 22. If, based on the signal direction of the detection signal, the foul air gas is the dominant gas, the electronic control unit 20 increases the controlling gas supply from the controlling gas source 12 to the foul air volume 22. "Reducing" and "increasing" the controlling gas supply, as used herein, can include, respectively, stopping and starting the supply of the controlling gas.

In FIG. 1, the foul air volume 22 is depicted generically. It will be appreciated that the odor control system 10 of the present invention can be advantageously employed with multiple types of foul air volumes. Additionally, a given odor control system 10 could be connected to more than one foul air volume in a given location, either using a single controlling gas source 12 and gas sensor module 14, or separate controlling gas sources and/or sensor modules.

Figure 6:
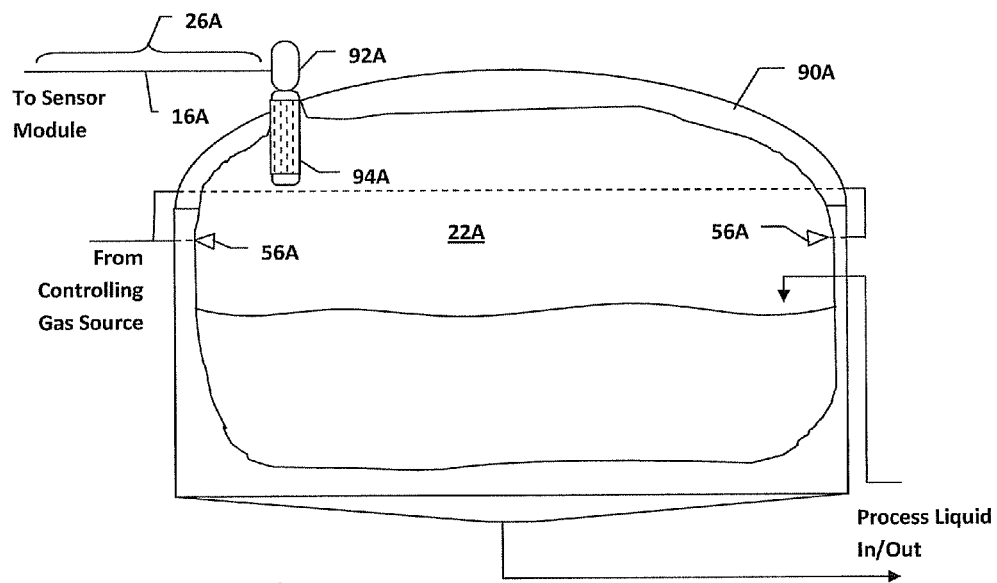
FIGS. 6-8 are partial cutaway views of foul air volumes deodorized by an odor control system, according to different embodiments of the present invention.

In the following foul air volume examples, similar components are referred to with similar reference numerals. Referring to FIG. 6, the foul air volume 22A is the airspace in a process holding tank 90A. The sample conduit 16A is connected to a vent 92A, having a slotted filter 94A to facilitate condensation of neutralized liquid fog. The reaction completion distance 26A is covered by the sample conduit 16A.

Figure 7:
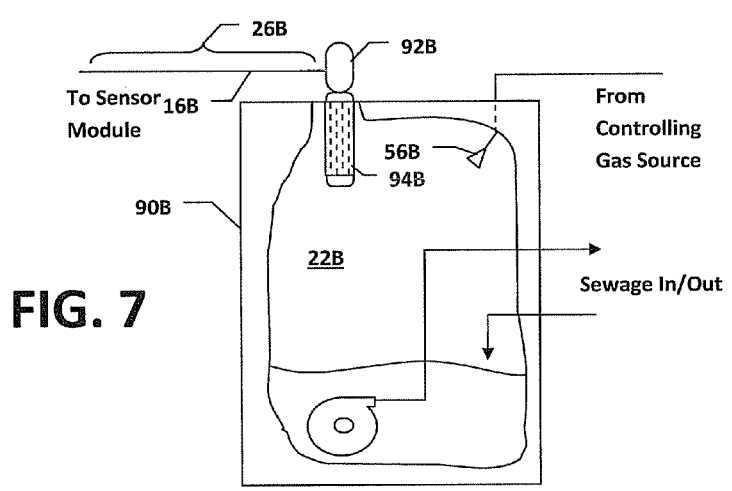

Referring to FIG. 7, the foul air volume 22B is the airspace in a sewage wet well 90B. The sample conduit 16B is again connected to a vent 92B, having a slotted filter 94B to facilitate condensation of neutralized liquid fog. The reaction completion distance 26B is covered by the sample conduit 16B.

Figure 8:
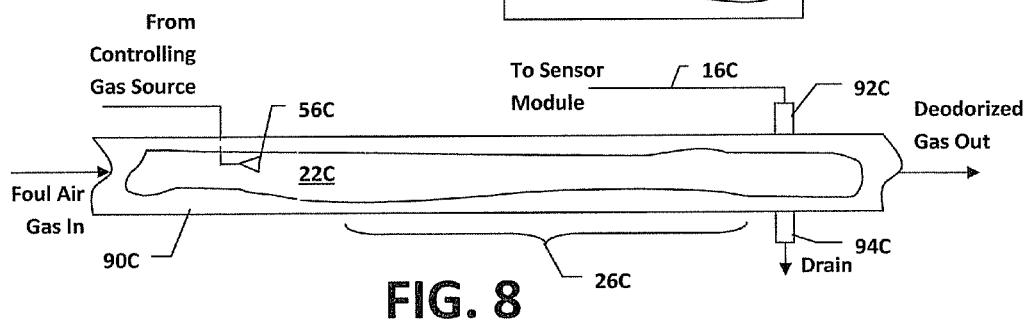

In FIG. 8, the foul air volume 22C is a foul air duct 90C. The sample conduit 16C taps off the duct at a port 92C, and drain port 94C drains condensate. The reaction completion distance 26C is covered within the foul air duct 90C, itself.

In general, the foregoing description is provided for exemplary and illustrative purposes; the present invention is not necessarily limited thereto. Rather, those skilled in the art will appreciate that additional modifications, as well as adaptations for particular circumstances, will fall within the scope of the invention as herein shown and described and the claims appended hereto.

What is claimed is:

1. A method of controlling odor from a foul air gas in a foul air volume using controlling gas from a controlling gas source, the method comprising:
    arranging a gas sensor module in a sample conduit connected to the foul air volume;
    setting a signal baseline of the gas sensor module, the signal baseline corresponding to a substantial absence of both the foul air gas and the controlling gas;
    detecting, with the gas sensor module, a dominant gas of the foul air gas and the controlling gas in the sample conduit;
    generating, with the gas sensor module, a detection signal based on the detection of the dominant gas, the detection signal having a positive or negative signal direction relative to the signal baseline indicative of whether the dominant gas is the foul air gas or the controlling gas, the signal direction when the dominant gas is the foul air gas being opposite the signal direction when the dominant gas is the controlling gas; and
    controlling, with an electronic control unit, the controlling gas source to adjust the supply of the controlling gas to the foul air volume in response to the detection signal.

2. The method of claim 1, wherein the controlling gas includes ozone.

3. The method of claim 2, wherein the foul air gas includes hydrogen sulfide.

4. The method of claim 3, wherein the gas sensor module includes a metal oxide sensor.

5. The method of claim 1, wherein setting the signal baseline includes supplying, via a selector valve, zero air to the gas sensor module through the sample conduit.

6. The method of claim 1, wherein arranging the gas sensor module in the sample conduit includes arranging the gas sensor module at least one reaction completion distance for the controlling gas and the foul air gas from the foul air volume.

7. The method of claim 1, wherein the foul air volume includes at least one of: a sewage holding tank, a sewage wet well and a foul air duct.

8. A method of controlling odor from a foul air gas in a foul air volume using controlling gas from a controlling gas source, the foul air gas including hydrogen sulfide and the controlling gas including ozone, the method comprising:
    arranging a gas sensor module in a sample conduit connected to the foul air volume;
    setting a signal baseline of the gas sensor module, the signal baseline corresponding to a substantial absence of both the hydrogen sulfide and ozone;
    detecting, with the gas sensor module, a dominant gas of the hydrogen sulfide and the ozone in the sample conduit;
    generating, with the gas sensor module, a detection signal based on the detection of the dominant gas, the detection signal having a positive or negative signal direction relative to the signal baseline indicative of whether the dominant gas is the hydrogen sulfide or the ozone, the signal direction when the dominant gas is the hydrogen sulfide being opposite the signal direction when the dominant gas is the ozone; and
    controlling, with an electronic control unit, the controlling gas source to adjust the supply of the ozone to the foul air volume in response to the detection signal.

9. The method of claim 8, wherein setting the signal baseline includes supplying, via a selector valve, zero air to the gas sensor module through the sample conduit.

* * * * *